United States Patent [19]
Sultan

[11] Patent Number: 6,148,824
[45] Date of Patent: Nov. 21, 2000

[54] METHOD FOR MOVING A PORTION OF A PARALYZED LIMB

[76] Inventor: Hashem Sultan, 8455 Island Pines Pl., Mainville, Ohio 45039

[21] Appl. No.: 08/879,801

[22] Filed: Jun. 20, 1997

[51] Int. Cl.[7] .................................................. A61B 19/00
[52] U.S. Cl. .............................................. 128/898; 602/5
[58] Field of Search ............................... 128/898; 602/5, 602/28; 473/213; 623/18, 21, 13–14, 66

[56] References Cited

U.S. PATENT DOCUMENTS

| | | | |
|---|---|---|---|
| 5,527,040 | 6/1996 | Stanley et al. | 473/213 |
| 5,542,912 | 8/1996 | Hess | 602/27 |
| 5,582,583 | 12/1996 | Ballantyne | 602/5 |
| 5,591,121 | 1/1997 | Cantrall | 602/5 |

*Primary Examiner*—Mickey Yu
*Assistant Examiner*—Kelly O'Hara
*Attorney, Agent, or Firm*—Wood, Herron & Evans, LLP

[57] ABSTRACT

A method of moving a portion of a limb which has been partially paralyzed, comprises implanting a biasing device in the body of a person having a limb which is at least partially paralyzed, and attaching one end of the biasing device to a first portion of the limb to be moved. Another end of the biasing device is anchored to a second portion of the limb. The biasing device is operable for biasing the first portion of the limb in a first direction to hold the first portion in a first position, and the biasing device is further operable for allowing the first portion to move in a second direction when a force from a non-paralyzed muscle group acts on the first portion of the limb. The biasing device continues to bias the first portion in the first direction so that the limb returns to the first position when the force from the muscle group is removed.

11 Claims, 5 Drawing Sheets

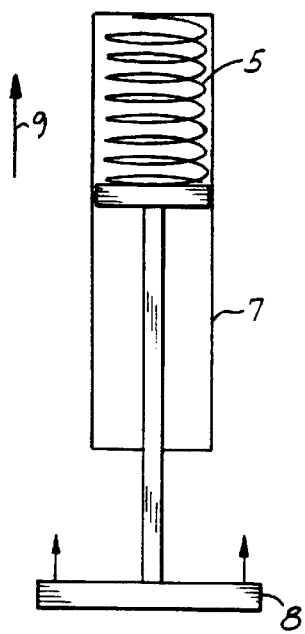
FIG. 2D1
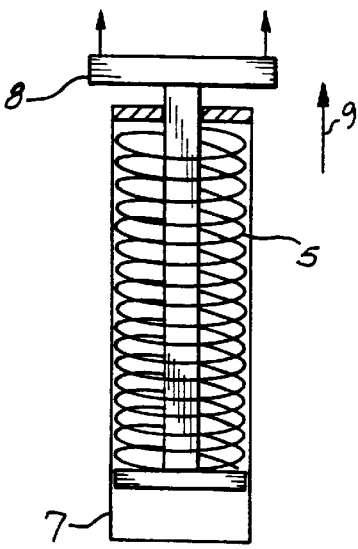
FIG. 2D2
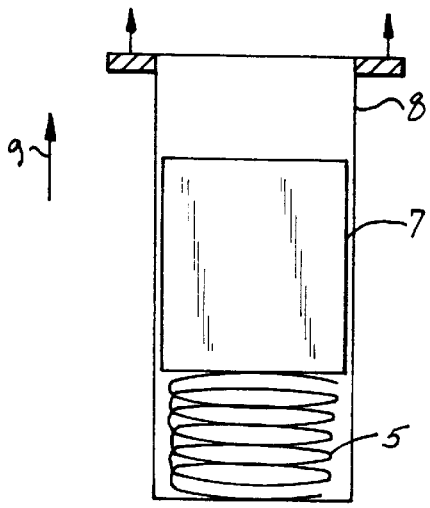
FIG. 2D3
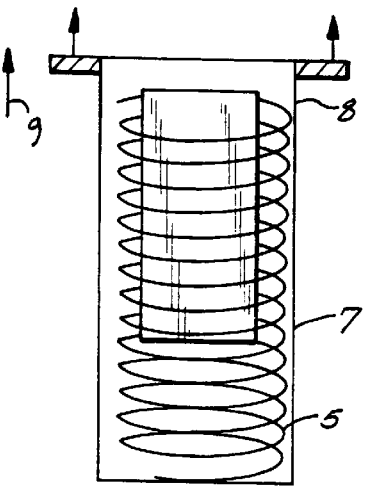
FIG. 2D4
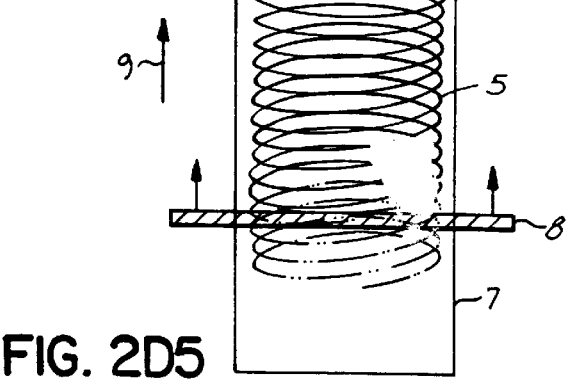
FIG. 2D5

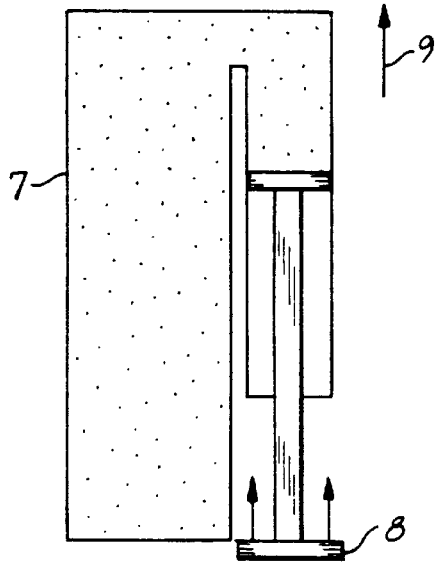
FIG. 2E1
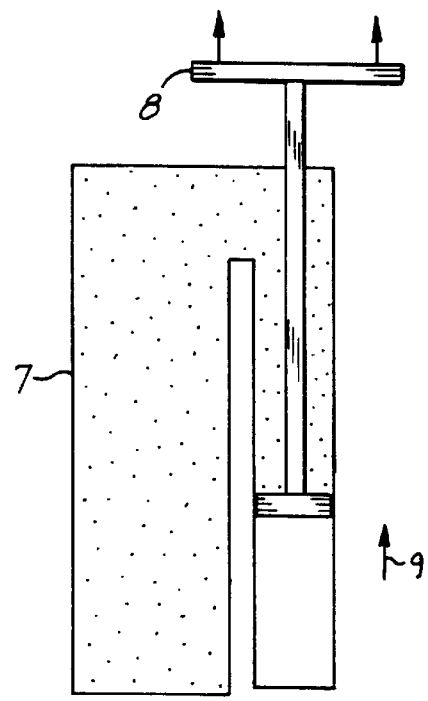
FIG. 2E2
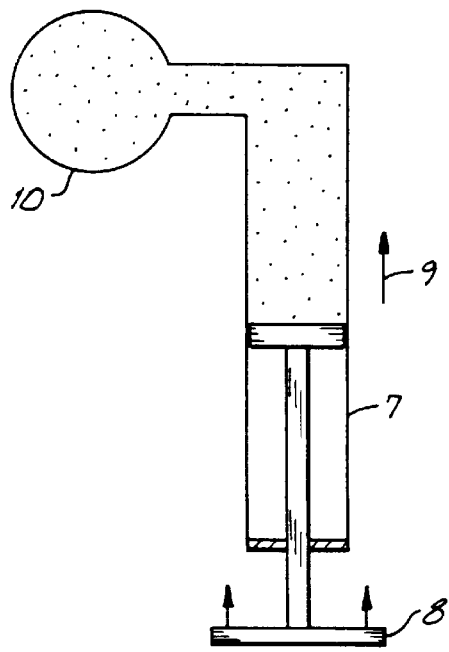
FIG. 2E3
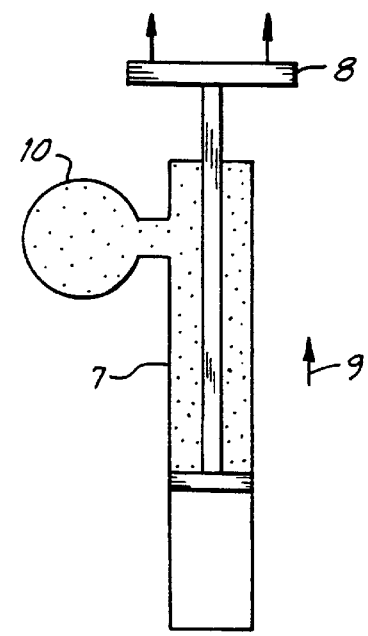
FIG. 2E4

METHOD FOR MOVING A PORTION OF A PARALYZED LIMB

BACKGROUND OF INVENTION

RELATED PRIOR ART

Tendon transfer is a surgical procedure in which a muscle tendon from the non-paralyzed muscle group is transferred to a tendon of the paralyzed muscle group to achieve some movement.

This procedure is one of few options available for the treatment of loss of motor function secondary to nerve injury those options are either operative or non operative.

The non operative options include external splinting. Examples of these splinting devices are disclosed in the following U.S. patents

- Patent # 5,591,121 Date 01.07.97.
- Patent # 5,582,583 Date 12.10.96.
- Patent # 5,542,912 Date 08.06.96.
- Patent # 5,527,040 Date 06.18.96.

Operative options, on the other hand, are limited to tendon transfer procedures.

Many tendon transfer variations have been described. All of those variations use the same principle of transferring a tendon of a non paralyzed muscle group to the paralyzed muscle group. They vary with the choice of the tendon to be transferred and the method of attachment to the paralyzed muscle.

Because of the relative satisfaction achieved with radian nerve tendon transfers, non operative (splinting) care can not be advocated for most patients. It can be useful while awaiting nerve recovery following nerve injury or after nerve repair.

Tendon transfer allows some function of the paralyzed muscle group, but owing to decrease in the strength of the non-paralyzed muscle group as a result of the tendon transfer, the overall benefit is not significant in most of the times The idea of this invention is to overcome the disadvantages of the above methods and provide a simple effective method to achieve the best results without the need for transferring a tendon.

The current device is best explained by example of radial nerve injury where patient lost the ability to extend the wrist but is able to flex the wrist normally.

The device will be implanted on the tendon that extend the wrist. By a spring-like action it will pull the extensor tendon or the distal bony edge of the wrist giving rise to wrist extension. Therefore, wrist extension will be simply a passive movement. Wrist flexion,on the other hand, will be simply achieved by actively moving the wrist by the non-paralyzed muscle group (The flexors).

The above function is very much similar to a door which is opened by a doorman and closed passively by a pulling spring. Opening and closing is therefor achieved by only one doorman whose job is only to open the door (Non-paralyzed muscle group). The pulling spring will close the door (The device of the new invention).

This new idea has not been used before. There are no references cited in literature or in patents.

SUMMARY OF INVENTION

The new invention is simply a biasing device which can be stretched by applying a pulling force and returns to its original length when the pulling force is eliminated.

It can be made of any substance, or contained in an envelope made of any substance, which does not cause adverse reaction to its implantation in the body.

The device comprises mainly a body and two ends. The first (distal) end is to be attached to the tendon of the paralyzed muscle or to the distal bony edge of the paralyzed joint. The second (proximal) end is to be attached to any tissue proximal to the attachment of the first end. The body can be made for example of a spring contained in a corrugated silastic tube.

The ability of the body to stretch on application of pulling forces (flexing the wrist for example) and to returns to its original length on stopping the pulling action can be achieved by the elastic property of the material (like elastic band), by a spring-like action (using a spring which may be contained in an envelop), by a small tube(s) that can work by a hydraulic mechanism, or by any other available material or mechanism that has similar elastic property

OBJECTS & ADVANTAGES

Accordingly, the present invention achieves several objects and advantages over the tendon transfer methods some of these are:

- provide a new alternative method of treating wrist drop or foot drop or similar medical conditions which requires tendon transfer surgery.
- Does not lead to weakening of the non-paralyzed muscle group.
- Patient will be able to use the joint immediately after surgery, in contrast to tendon transfer which requires postop splinting and then rehabilitation.
- Can be used in patients who are awaiting the recovery of their nerve function after nerve injury.
- Simplicity of the implantation technique.

BRIEF DESCRIPTION OF THE DRAWINGS

FIGS. 2A1 and 2A2 are view of embodiments of a biasing device for use in the method of the invention.

FIG. 2d1 is a cross-sectional view of another embodiment of a biasing device for use in the method of the invention.

FIG. 2d2 is a cross-sectional view of another embodiment of a biasing device for use in the method of the invention.

FIG. 2d3 is a cross-sectional view of another embodiment of a biasing device for use in the method of the invention.

FIG. 2d4 is a cross-sectional view of another embodiment of a biasing device for use in the method of the invention.

FIG. 2d5 is a cross-sectional view of another embodiment of a biasing device for use in the method of the invention.

FIGS. 2E1, 2E2, 2E3, and 2E4 are cross-sectional views of other embodiments of a biasing device for use in the method of the invention utilizing a hydraulic mechanism.

FIG. 4 is a representative method of implantation of a biasing device for the present invention.

Figure 1:
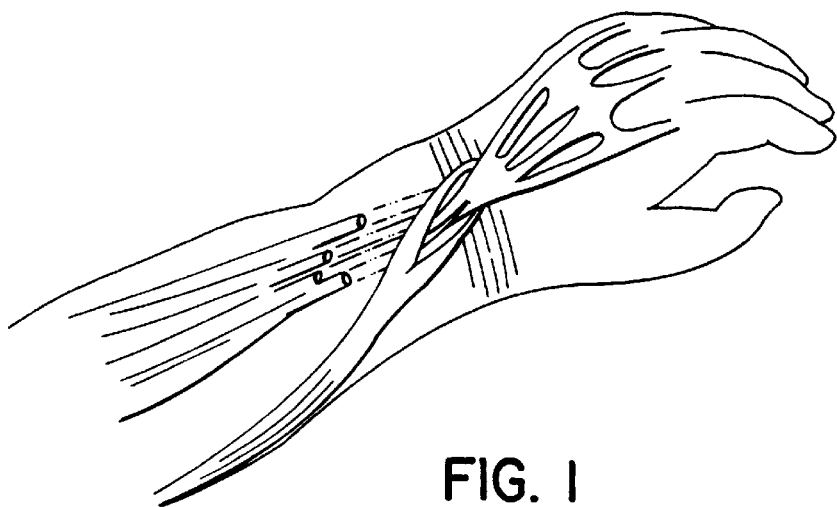
FIG. 1 is a perspective cross-sectional view of a traditional method of tendon transfer.

REFERENCE NUMERALS IN DRAWINGS 1 proximal end.
2 Distal end.
3 Body.
4 Envelope.
5 Spring.
6 Holes for attaching the device to the tissues.
7 Fixed part.
8 Movable part.
9 Arrow indicating the direction of the pulling force.
10 Distend able device under filling pressure (like a balloon) with tendency to collapse

DETAILED DESCRIPTION OF THE INVENTION

FIG. 1 illustrates the end result of tendon transfer procedures. The tendon of a muscle of the non-paralyzed muscle group, flexor carpi radialis muscle is routed subcutaneously around the radial forearm to join the tendons of the paralyzed muscle which have been sectioned proximally, drawn distally to be sutured on the tendon of the paralyzed muscle.

FIG. 2 illustrates examples of the biasing device. FIG. 2A comprises mainly a spring of sufficient strength and elasticity (5) contained in a corrugated envelop (5) or an elastic envelope made of a material that does not cause adverse reaction to its implantation in the tissue, like silastic.

Both ends (1, 2) of the spring and the envelop are fused or firmly adherent to each other. Holes (6) are optional but preferable as they facilitate the application of sutures or screws through the device.

Figure 2B:
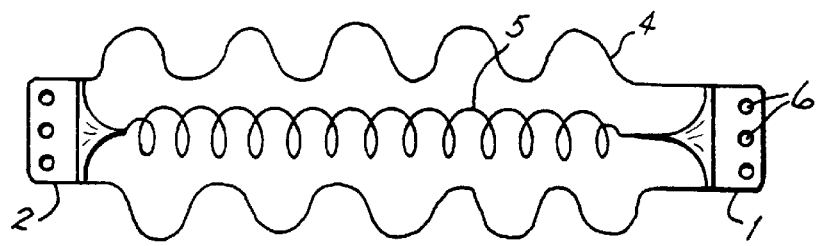
FIG. 2b is a view of one embodiment of a biasing device for use in the method of the invention.
Figure 2B:
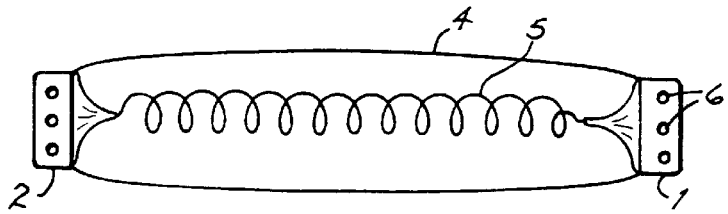
Figure 2B:

FIG. 2B illustrate the biasing device made simply of a spring made of a material that does not cause reaction to its implantation in the body.

Figure 2C:
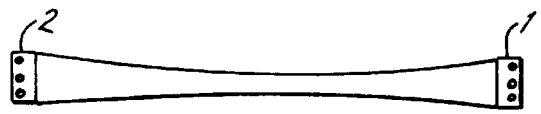
FIG. 2c is a view of one embodiment of a biasing device for use in the method of the invention.

FIG. 2C illustrate the biasing device as being an elastic band made of non reactive nontoxic material.

FIG. 2D illustrate a form of the biasing device made up of a fixed part (7) and a movable part (8). The movable part is pulled when the joint is actively moved and returns to its original position by a spring (5) contained in the device.

Two basic types of function of this device can be made depending whether the active pulling on the movable part causes stretching versus compressing of the spring. FIG. 2D 1,2,3,4,5.

FIG. 2E Illustrate a form of the biasing device with a hydraulic mechanism.

FIG. 3 Illustrates the various methods of implanting the device in wrist drop:
tissues—tendon: The proximal end is fixed to the tissues proximal to the wrist and the distal end is fixed on the extensors of the wrist and fingers.
Tendon—tendon: Both ends of the device is fixed to the extensors of the wrist and fingers along its length.
across the wrist: The distal end of the device is fixed to the distal bony edge of the wrist.
FIG. 4 Illustrates the implantation of the device in foot drop.

Figure 3A:
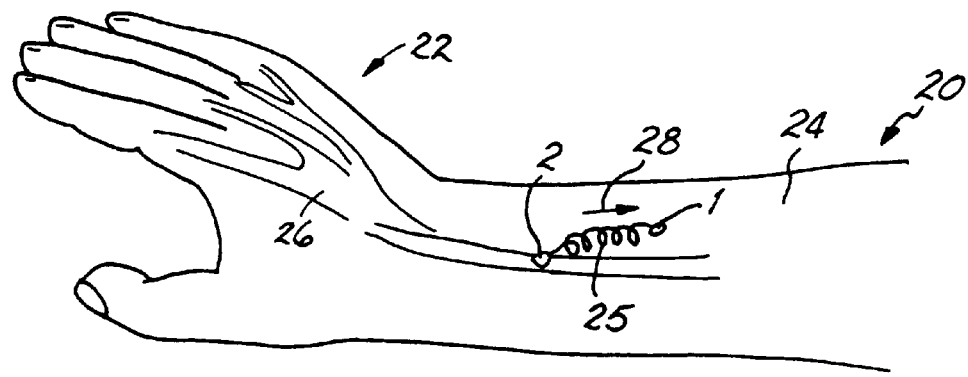
FIG. 3a is a representative method of implantation of a biasing device for the present invention.

Specifically, referring to FIG. 3, an arm 20 is shown, and specifically a hand 22 and wrist area 24 are illustrated. As noted above, and in accordance with one embodiment of the present invention, one example of a biasing device 25 is utilized to be coupled between an anchor position and tendons of a paralyzed muscle 26. As discussed hereinabove with respect to FIG. 1, the tendons 26 could be extensors of the wrist and fingers, as illustrated in FIG. 3A. The proximal end 1 is fixed to tissues proximal to the wrist. The distal end of device 25 is fixed to the extensors of the wrist and fingers 26. In that way, the device 25 biases the wrist and finger extensors in the direction of arrow 28. Flexing of the hand or wrist in the opposite direction will be achieved by the operable muscle and tendon groups.

Figure 3B:
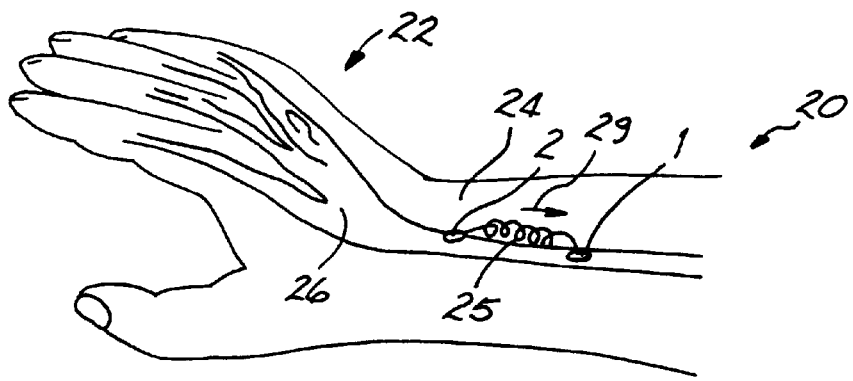
FIG. 3b is a representative method of implantation of a biasing device for the present invention.
Figure 4:
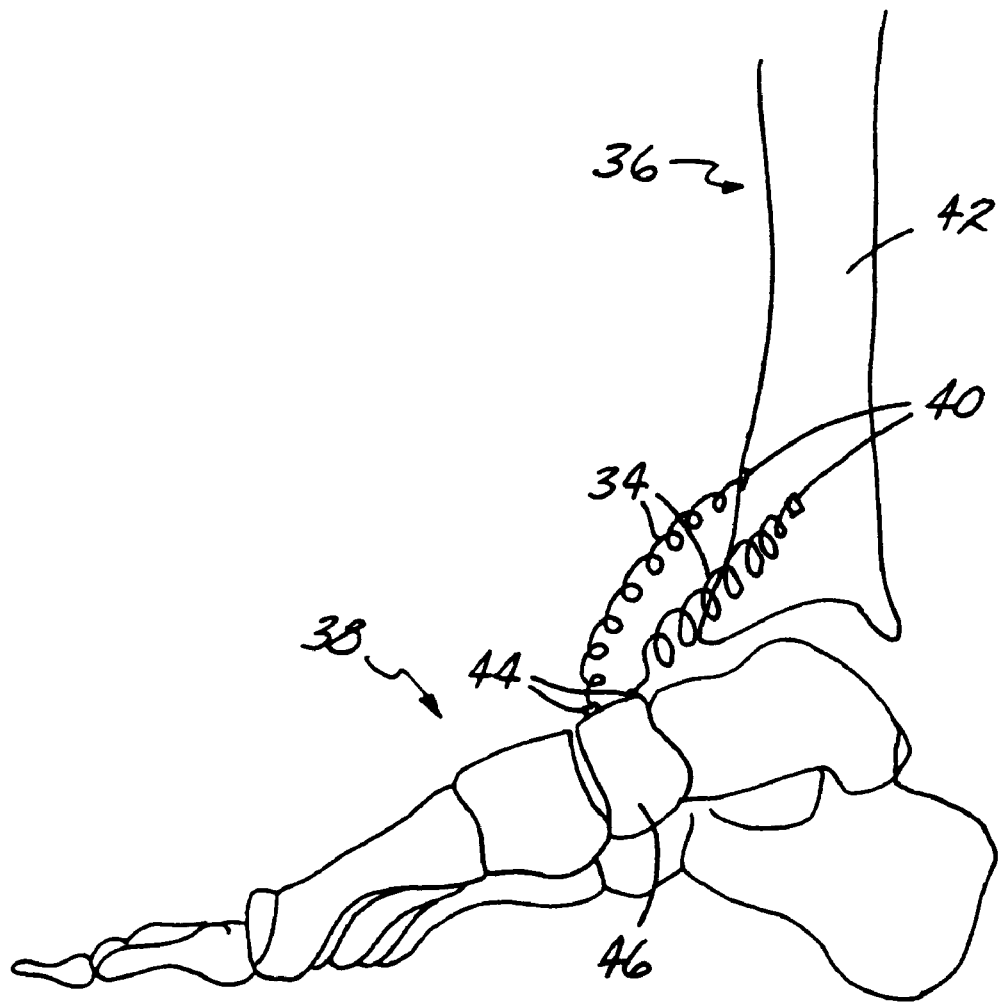

FIG. 3B illustrates another embodiment of the invention wherein both the proximal and distal ends 1, 2 of the device 25 are fixed to the extensors of the wrist and fingers 26 along its length. In that way, device 25 biases the wrist and fingers in direction of arrow 29.

Figure 3C:
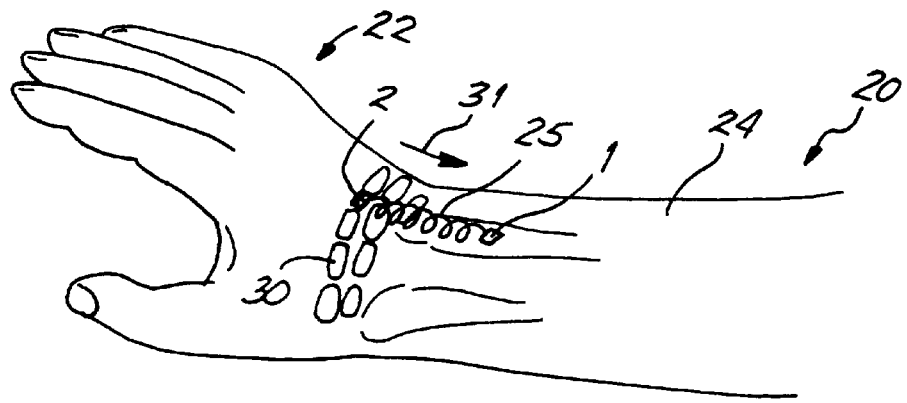
FIG. 3c is a representative method of implantation of a biasing device for the present invention.

FIG. 3C illustrates an arm portion 20 as shown in FIGS. 3A and 3B wherein the biasing device 25 is coupled across the wrist. Specifically, the proximal end of device 25 is coupled to tissues proximal to the wrist, as illustrated in FIG. 3C. The distal end 2 of device 25 is then fixed to the distal bony edge 30 of the wrist. In that way, the biasing device 25 biases the hand and wrist in the direction of arrow 31.

Referring specifically to FIG. 4, an embodiment of the invention as illustrated is utilized to correct foot drop. Specifically, one or more biasing devices 34 might be utilized between a leg 36 and foot 38 of a patient. Specifically, proximal ends 40 of the devices 34 are coupled to a leg bone 42 and related tissue, while distal ends of the devices 34 are coupled to a foot bone 46 and related tissue.

The embodiments of the biasing devices 25 and 34 illustrated in FIGS. 3 and 4 are shown as spring-like types of the biasing device. However, other forms of the biasing devices disclosed hereinabove might be utilized according to the inventive methods described with respect to FIGS. 3 and 4.

I claim:

1. A method of moving a portion of a limb which has been partially paralyzed, the method comprising:
    implanting a biasing device in the body of a person having a limb which is at least partially paralyzed;
    attaching one end of the biasing device to a first portion of the limb to be moved;
    anchoring another end of the biasing device to a second portion of the limb;
    the biasing device operable for biasing the first portion of the limb in a first direction to hold said first portion in a first position, the biasing device further operable for allowing the first portion to move in a second direction when a force from a non-paralyzed muscle group acts on said first portion of the limb while continuing to bias the first portion in said first direction so that it returns to said first position when the force from the muscle group is removed.

2. The method of claim 1 wherein said biasing device includes a spring device for biasing the first portion in said first direction, the spring device deflecting when the first portion is moved in the second direction and returning to an original shape when the first portion returns to said predetermined position.

3. The method of claim 2 wherein said spring device includes a coil spring.

4. The method of claim 2 wherein said spring device includes an elastic band.

5. The method of claim 1 wherein said implantation step includes implanting the biasing device in a envelope made of a nontoxic material that does not cause adverse reactions in the body.

6. The method of claim 1 wherein said biasing device includes a case and a piston movable therein, said biasing device further including a spring coupled between the case and piston, the spring being deflected when the piston is moved in one direction by said force and biasing the piston in an opposite direction against said force;

the attaching step further comprising:

attaching one of said case and said piston to a first portion of the limb to be moved; and the anchoring step further comprising:

anchoring the other of said case and piston to a second portion of the limb.

7. The method of claim 1 wherein said biasing device includes a case and a piston movable therein, said biasing device further including a liquid contained in the case and fluidly coupled with the piston, the fluid being compressed when the piston is moved in one direction by said force, the compressed fluid biasing the piston in an opposite direction against said force;

the attaching step further comprising:

attaching one of said case and said piston to a first portion of the limb to be moved; and the anchoring step further comprising:

anchoring the other of said case and piston to a second portion of the limb.

8. The method of claim 1 wherein said biasing device includes a case and a piston movable therein, said biasing device further including a gas contained in the case and pneumatically coupled with the piston, the gas being compressed when the piston is moved in one direction by said force, the compressed gas biasing the piston in an opposite direction against said force;

the attaching step further comprising:

attaching one of said case and said piston to a first portion of the limb to be moved; and the anchoring step further comprising:

anchoring the other of said case and piston to a second portion of the limb.

9. The method of claim 1 wherein said one end of the biasing device is attached to tissues of the limb and the other end of the device is attached to a tendon of the limb.

10. The method of claim 1 wherein said one end of the biasing device is attached to a tendon of the limb and the other end of the device is attached to a tendon of the limb.

11. The method of claim 1 wherein said one end of the biasing device is attached to a tendon of the limb and the other end of the device is attached to a bone portion of the limb.

\* \* \* \* \*